United States Patent [19]

Skuballa et al.

[11] Patent Number: 5,783,602
[45] Date of Patent: Jul. 21, 1998

[54] LEUKOTRIENE-B4 DERIVATIVES, PROCESS FOR THEIR PRODUCTION AND THEIR USE AS PHARMACEUTICAL AGENTS

[75] Inventors: Werner Skuballa; Bernd Buchmann; Josef Heindl; Wolfgang Fröhlich; Roland Ekerdt; Claudia Giesen, all of Berlin, Germany

[73] Assignee: Schering Aktiengesellschaft, Berlin, Germany

[21] Appl. No.: 682,699

[22] PCT Filed: Jan. 27, 1994

[86] PCT No.: PCT/EP94/00215

§ 371 Date: Dec. 4, 1996

§ 102(e) Date: Dec. 4, 1996

[87] PCT Pub. No.: WO95/20563

PCT Pub. Date: Aug. 3, 1995

[51] Int. Cl.[6] .................... C07C 59/54; A61K 31/557
[52] U.S. Cl. .................... 514/557; 514/570; 560/118; 560/121; 562/470; 562/500; 562/503; 564/171
[58] Field of Search .................... 560/121, 118; 562/503, 470, 500; 564/171; 514/570, 557

[56] References Cited

FOREIGN PATENT DOCUMENTS 4242390  6/1994  Germany .................... 560/121

*Primary Examiner*—Robert Gerstl
*Attorney, Agent, or Firm*—Millen, White, Zelano & Branigan, P.C.

[57] ABSTRACT

The invention relates to leukotriene-$B_4$ derivatives of general formula I,

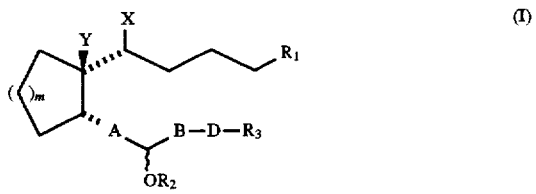

(I)

in which $R_1$ represents $CH_2OH$, $CH_3$, $CF_3COOR_4CONR_5R_6$, and $R_3$ symbolizes H; $C_1$–$C_{14}$ alkyl, $C_3$–$C_{10}$ cycloalkyl optionally substituted singly or multiply; $C_6$–$C_{10}$ aryl radicals, independently of one another, optionally substituted singly or multiply by halogen, phenyl, $C_1$–$C_4$ alkyl, $C_1$–$C_4$ alkoxy, fluoromethyl, chloromethyl, trifluoromethyl, carbonyl, carboxyl or hydroxy; or a 5- to 6-membered aromatic heterocyclic ring with at least 1 heteroatom, X and Y mean a direct bond, whereby the resulting olefin can be E- or Z-configured or X represents a fluorine atom in α- or β-position, and Y means a hydrogen atom in β-position.

3 Claims, No Drawings

LEUKOTRIENE-B4 DERIVATIVES, PROCESS FOR THEIR PRODUCTION AND THEIR USE AS PHARMACEUTICAL AGENTS

The invention relates to new leukotriene-$B_4$ derivatives, process for their production and their use as pharmaceutical agents. The new compounds are optically active structural analogues of previously known leukotriene-$B_4$ antagonists, which contain a six-membered ring as a basic structural element (DE-A 39 17 597, DE-A 42 27 790.6). Leukotriene $B_4$ ($LTB_4$) discovered by B. Samuelsson et al. as a metabolite of the arachidonic acid. In the biosynthesis, leukotriene $A_4$ is formed the enzyme 5-lipoxygenase first as a central intermediate duct, which then is converted by a specific hydrolase to the $LTB_4$.

for inflammatory diseases, in which leukocytes invade the affected tissue.

The effects of $LTB_4$ are triggered on the cellular plane by the bond of $LTB_4$ on a specific receptor.

It is known concerning $LTB_4$ that it causes the adhesion of leukocytes on the blood vessel wall. $LTB_4$ is chemotactically effective, i.e., it triggers a directed migration of leukocytes in the direction of a gradient of increasing concentration. Furthermore, it indirectly changes the vascular permeability based on its chemotactic activity, and a synergism with prostaglandin $E_2$ is observed. $LTB_4$ obviously plays a decisive role in inflammatory, allergic and immunological processes.

Leukotrienes and especially $LTB_4$ are involved in skin diseases, which are accompanied by inflammatory processes (increased vascular permeability and formation of edemas,

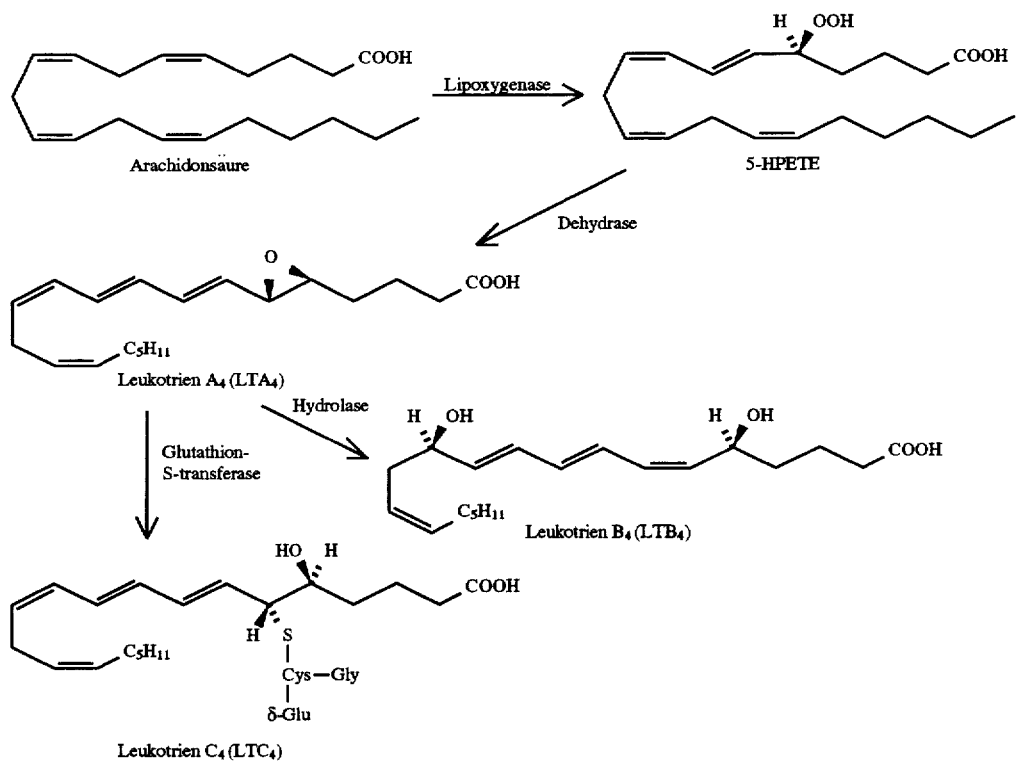

KEY:

Arachidonsäure=arachidonic acid
Leukotrien $A_4$ ($LTA_4$)=leukotriene $A_4$ ($LTA_4$)
Glutathion - S-transferase=glutathione - S-transferase
Leukotrien $B_4$ ($LTB_4$)=leukotriene $B_4$ ($LTB_4$)
Leukotrien $C_4$ ($LTC_4$)=leukotriene $C_4$ ($LTC_4$)

The nomenclature of the leukotrienes can be gathered from the following works:

a) B. Samuelsson et al., Prostaglandins 19, 645 (1980); 17, 785 (1979).

b) C. N. Serhan et al., Prostaglandins 34, 201 (1987).

The physiological and especially the pathophysiological importance of leukotriene $B_4$ is summarized in several more recent works: a) The Leukotrienes, Chemistry and Biology eds. L. W. Chakrin, D. M. Bailey, Academic Press 1984. b) J. W. Gillard et al., Drugs of the Future 12, 453 (1987). c) B. Samuelsson, Sciences 237, 1171 (1987). d) C. W. Parker, Drug Development Research 10, 277 (1987). It follows from the above that $LTB_4$ is an important inflammation mediator cell infiltration), increased proliferation of skin cells and itching, such as, for example, in eczemas, erythemas, psoriasis, pruritus and acne. Pathologically increased leukotriene concentrations are involved either causally in the development of many dermatitides or there is a connection between the persistence of the dermatitides and the leukotrienes. Clearly increased leukotriene concentrations were measured, for example, in the skin of patients with psoriasis or atopic dermatitis.

Leukotrienes and especially $LTB_4$ are also involved in the diseases of internal organs, for which an acute or chronic inflammatory component was described, e.g.: joint diseases (arthritis); diseases of the respiratory tract (asthma, rhinitis and allergies); inflammatory intestinal diseases (colitis); as well as reperfusion damages (to the heart, intestinal or renal tissues), which result by the temporary pathological obstruction of blood vessels.

Further, leukotrienes and especially $LTB_4$ are involved in the disease of multiple sclerosis and in the clinical picture of shock (triggered by infections, burns or in complications in kidney dialysis or other separately discussed perfusion techniques).

Leukotrienes and especially LTB$_4$ further have an effect on the formation of white blood cells in the bone marrow, on the growth of unstriped muscle cells, of keratinocytes and of B-lymphocytes. LTB$_4$ is therefore involved in diseases with inflammatory processes and in diseases with pathologically increased formation and growth of cells.

For example, leukemia or arteriosclerosis represent diseases with this clinical picture.

By the antagonizing of the effects, especially by LTB$_4$, the active ingredients and their forms of administration of this invention are specific medicines for diseases of humans and animals, in which especially leukotrienes play a pathological role.

Besides the therapeutic possibilities, which can be derived from an antagonizing of LTB$_4$ action with LTB$_4$ analogues, the usefulness and potential use of leukotriene-B$_4$ agonists for the treatment of fungus diseases of the skin were also able to be shown (H. Katayama, Prostaglandins 34, 797 (1988)).

The invention relates to leukotriene-B$_4$ derivatives of general formula I

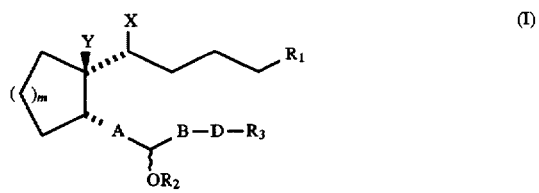

in which $R_1$ represents $CH_2OH$, $CH_3$, $CF_3$, $COOR_4$, $CONR_5R_6$, and $R_2$ represents H or an organic acid radical with 1–15 C atoms, $R_3$ symbolizes H; $C_1$–$C_{14}$ alkyl, $C_3$–$C_{10}$ cycloalkyl optionally substituted singly or multiply; $C_6$–$C_{10}$ aryl radicals, independently of one another, optionally substituted singly or multiply by halogen, phenyl, $C_1$–$C_4$ alkyl, $C_1$–$C_4$ alkoxyl, fluoromethyl, chloromethyl, trifluoromethyl, carbonyl, carboxyl or hydroxy; or a 5-to 6-membered aromatic heterocyclic ring with at least 1 heteroatom.

$R_4$ means hydrogen, $C_1$–$C_{10}$ alkyl, $C_3$–$C_{10}$ cycloalkyl; $C_6$–$C_{10}$ aryl radicals optionally substituted by 1–3 halogen, phenyl, $C_1$–$C_4$ alkyl, $C_1$–$C_4$ alkoxy, fluoromethyl, chloromethyl, trifluoromethyl, carboxyl or hydroxy; $CH_2$—$CO$—($C_6$–$C_{10}$) aryl or a 5- to 6-membered ring with at least 1 heteroatom.

A symbolizes a trans, trans—CH═CH—CH═CH, a —CH$_2$CH$_2$—CH═CH—or a tetramethylene group.

B symbolizes a $C_1$–$C_{10}$ straight-chain or branched-chain alkylene group, which optionally can be substituted by fluorine or the group

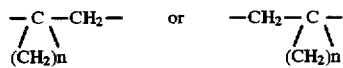

D means a direct bond, oxygen, sulfur, —C≡C—, —CH═CR$_7$, or together with B can also mean a direct bond, $R_5$ and $R_6$ are the same or different, and represent H or $C_1$–$C_4$ alkyl optionally substituted by hydroxy groups or $R_6$ represents H and $R_5$ represents $C_1$–$C_{15}$ alkanoyl or $R_8SO_2$, and optionally are substituted with OH, $R_7$ means H, $C_1$–$C_5$ alkyl, chlorine, bromine, $R_8$ has the same meaning as $R_3$, m means 1–3, n is 2–5, and, if $R_4$ means hydrogen, their salts with physiologically compatible bases and their cyclodextrin clathrates, X and Y mean a direct bond, whereby the resulting olefin can be E- or Z-configured or X represents a fluorine atom in α- or β-position, and Y means a hydrogen atom in β-position.

The group OR$_2$ can be in α- or β-position. Formula I comprises both racemates and the possible pure diastereomers and enantiomers.

As alkyl groups $R_4$, straight-chain or branched-chain alkyl groups with 1–10 C atoms are considered, such as, for example, methyl, ethyl, propyl, butyl, isobutyl, tert-butyl, pentyl, neopentyl, hexyl, heptyl, decyl.

Alkyl groups $R_4$ can optionally be substituted singly to multiply by halogen atoms, alkoxy groups, optionally substituted aryl or aroyl groups with 6–10 C atoms (relative to possible substituents, see under aryl $R_4$), dialkylamino and trialkylammonium with 1–4 C atoms in the alkyl portion, whereby the single substitution is to be preferred. As substituents, for example, fluorine, chlorine or bromine, phenyl, dimethylamino, diethylamino, methoxy, ethoxy can be mentioned. As preferred alkyl groups $R_4$, those with 1–4 C atoms can be mentioned.

Cycloalkyl group $R_4$ can contain 3–10, preferably 5 and 6 carbon atoms in the ring. The rings can be substituted by alkyl groups with 1–4 carbon atoms. For example, cyclopentyl, cyclohexyl, methylcyclohexyl can be mentioned.

As aryl groups $R_4$, both substituted and unsubstituted aryl groups with 6–10 C atoms are considered, such as, for example, phenyl, 1-naphthyl and 2-naphthyl, which can be substituted in each case by 1–3 halogen atoms (F, Cl, Br), a phenyl group, 1–3 alkyl groups with, in each case, 1–4 C atoms, a chloromethyl, a fluoromethyl, trifluoromethyl, carboxyl, hydroxy or alkoxy group with 1–4 C atoms. Preferred substituents in 3- and 4-position on the phenyl ring are, for example, fluorine, chlorine, alkoxy or trifluoromethyl, in 4-position, however, hydroxy.

As heterocyclic groups $R_4$, 5- and 6-membered aromatic heterocycles are suitable, which contain at least 1 heteroatom, preferably nitrogen, oxygen or sulfur. For example, 2-furyl, 2-thienyl, 2-pyridyl, 3-pyridyl, 4-pyridyl, oxazolyl, thiazolyl, pyrimidinyl, pyridazinyl, 3-furyl, 3-thienyl, 2-tetrazolyl, i.a., can be mentioned.

As acid radical $R_5$, such physiologically compatible acids are suitable. Preferred acids are organic carboxylic acids and sulfonic acids with 1–15 carbon atoms, which belong to the aliphatic, cycloaliphatic, aromatic, aromatic-aliphatic and heterocyclic series. These acids can be saturated, unsaturated and/or polybasic and/or substituted in the usual way. As examples of the substituents, $C_{1-4}$ alkyl, hydroxy, $C_{1-4}$ alkoxy, oxo or amino groups or halogen atoms (F, Cl, Br) can be mentioned. For example, the following carboxylic acids can be mentioned: formic acid, acetic acid, propionic acid, butyric acid, isobutyric acid, valeric acid, isovaleric acid, caproic acid, oenanthic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, cyclopropylacetic acid, cyclopentylacetic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-, di- and trichloroacetic acid, aminoacetic acid, diethylaminoacetic acid, piperidinoacetic acid, morpholinoacetic acid, lactic acid, succinic acid, adipic acid, benzoic acid; benzoic acids substituted with halogen (F, Cl, Br) or trifluoromethyl, hydroxy, $C_{1-4}$ alkoxy or carboxy groups; nicotinic acid, isonicotinic acid, furan-2-carboxylic acid, cyclopentylpropionic acid. As preferred arylsulfonyl radicals and alkanesulfonyl radicals $R_8SO_2$, those are to be considered that are derived from a sulfonic acid with up to 10 carbon atoms. As sulfonic acids, for example, methanesulfonic acid, ethanesulfonic acid, isopropanesulfonic acid, β-chloroethanesulfonic acid, butanesulfonic acid, cyclopentanesulfonic acid, cyclohexanesulfonic acid, benzenesulfonic acid, p-toluenesulfonic acid, p-chlorobenzenesulfonic acid, N, N-dimethylaminosulfonic acid, N, N-diethylaminosulfonic acid, N, N-bis-(β-chloroethyl)-aminosulfonic acid, N, N-diisobutylaminosulfonic acid, N, N-dibutylaminosulfonic acid, pyrrolidino, piperidino, piperazino, M-methylpiperazino and morpholinosulfonic acid are suitable.

As alkyl groups $R_3$, straight-chain and branched-chain, saturated and unsaturated alkyl radicals, preferably saturated, with 1–14, especially 1–10 C atoms, are suitable, which optionally can be substituted by optionally substituted phenyl (for substitution, see under aryl $R_5$). For example, methyl, ethyl, propyl, butyl, isobutyl, tert-butyl, pentyl, hexyl, heptyl, octyl, butenyl, isobutenyl, propenyl, pentenyl, benzyl, m- and p-chlorobenzyl groups can be mentioned. If alkyl groups $R_3$ are halogen-substituted, fluorine, chlorine and bromine are suitable as halogens.

As examples of halogen-substituted alkyl groups $R_3$, alkyls with terminal trifluoromethylene groups are considered.

Cycloalkyl group $R_3$ can contain 3–10, preferably 3–6 carbon atoms in the ring. The rings can be substituted by alkyl groups with 1–4 carbon atoms optionally by halogens. For example, cyclopropyl, cyclobutyl, cyclopentyl, cyclohexyl, methyl-cyclohexyl, fluorocyclohexyl can be mentioned.

As substituted or unsubstituted aryl groups $R_3$, for example, phenyl, 1-naphthyl and 2-naphthyl, which can be substituted in each case by 1–3 halogen atoms (F, Cl, Br), a phenyl group, 1–3 alkyl groups with 1–4 C atoms in each case, a chloromethyl, fluoromethyl, trifluoromethyl, carboxyl, $C_1$–$C_4$ alkoxy or hydroxy group, are considered. Preferred is the substitution in 3- and 4-position on the phenyl ring by, for example, fluorine, chlorine, alkoxy or trifluoromethyl or in 4-position by hydroxy.

As heterocyclic aromatic groups $R_3$, 5- and 6-membered heterocycles that contain at least 1 heteroatom, preferably nitrogen, oxygen or sulfur, are suitable. For example, 2-furyl, 2-thienyl, 2-pyridyl, 3-pyridyl, 4-pyridyl, oxazolyl, thiazolyl, pyrimidinyl, pyridazinyl, pyrazinyl, 3-furyl, 3-thienyl, i.a., can be mentioned.

As alkylene group B, straight-chain or branched, saturated or unsaturated alkylene radicals, preferably saturated with 1–10, especially with 1–5 C atoms, are suitable, which optionally can be substituted by fluorine atoms. For example, methylene, fluoromethylene, difluoromethylene, ethylene, 1, 2-propylene, ethylethylene, trimethylene, tetramethylene, pentamethylene, 1, 2-difluoroethylene, 1-fluoroethylene, 1-methyltetramethylene, 1-methyl-trimethylene, 1-methylene-ethylene, 1-methylene-tetramethylene can be mentioned.

Alkylene group B can further represent the group

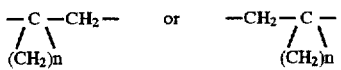

whereby n=2–5, preferably 3–5.

As acid radicals $R_2$, those of physiologically compatible acid radicals are suitable. Preferred acids are organic carboxylic acids and sulfonic acids with 1–15 carbon atoms, which belong to the aliphatic, cycloaliphatic, aromatic, aromatic-aliphatic or heterocyclic series. These acids can be substituted saturated, unsaturated and/or polybasic and/or in the usual way. As examples of the substituents, $C_{1-4}$ alkyl, hydroxy, $C_{1-4}$ alkoxy, oxo or amino groups or halogen atoms (F, Cl, Br) can be mentioned. For example, the following carboxylic acids can be mentioned: formic acid, acetic acid, propionic acid, butyric acid, isobutyric acid, valeric acid, isovaleric acid, caproic acid, oenanthic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, cyclopentylacetic acid, cyclohexylacetic acid, cyclohexanecarboxylic acid, phenylacetic acid, phenoxyacetic acid, methoxyacetic acid, ethoxyacetic acid, mono-, di- and trichloroacetic acid, aminoacetic acid, diethylaminoacetic acid, piperidinoacetic acid, morpholinoacetic acid, lactic acid, succinic acid, adipic acid, benzoic acid; benzoic acids substituted with halogen (F, Cl, Br) or trifluoromethyl, hydroxy, $C_{1-4}$ alkoxy or carboxy groups; nicotinic acid, isonicotinic acid, furan-2-carboxylic acid, cyclopentylpropionic acid. As preferred acid radicals $R_2$ and $R_3$, those acyl radicals with up to 10 carbon atoms are considered.

Alkyl radicals $R_5$ and $R_6$, which optionally contain hydroxy groups, are straight-chain or branched alkyl radicals, especially straight-chain, such as, for example, methyl, ethyl, propyl, butyl, pentyl, hexyl, especially preferably methyl.

$R_7$ as $C_{1-5}$ alkyl means straight-chain or branched-chain alkyl radicals as were already mentioned for $R_3$ or $R_4$. Preferred alkyl radicals $R_7$ are methyl, ethyl, propyl and isopropyl.

Inorganic and organic bases are suitable for salt formation, as they are known to one skilled in the art for forming physiologically compatible salts. For example, alkali hydroxides, such as sodium hydroxide and potassium hydroxide, alkaline-earth hydroxides, such as calcium hydroxide, ammonia, amines, such as ethanolamine, diethanolamine, triethanolamine, N-methylglucamine, morpholine, tris-(hydroxymethyl)-methylamine, etc., can be mentioned.

To attain the cyclodextrin clathrates, the compounds of formula I are reacted with α-, β- or γ-cyclodextrin. Preferred are β-cyclodextrin derivatives.

Preferred compounds of this invention are compounds of general formula I, whereby the radicals have the following meaning:

$R_1$ is $CH_2OH$, $CONR_5R_6$, $COOR_4$ with $R_4$ meaning a hydrogen atom, an alkyl radical with 1–10 C atoms, a cycloalkyl radical with 5–6 C atoms, a phenyl radical optionally substituted by 1–2 chlorine, bromine, phenyl, $C_{1-4}$ alkyl, $C_{1-4}$ alkoxy, chloromethyl, fluoromethyl, trifluoromethyl, carboxy or hydroxy, m is 1–3, A is a trans—CH=CH—CH=CH or tetramethylene group;

B is a straight-chain or branched-chain, saturated or unsaturated alkylene group with up to 10 C atoms, which optionally can be substituted by fluorine, or the group

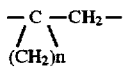

with n=2–5;

D is a direct bond, oxygen, sulfur, a —C≡C group or a —CH=CR$_7$ group with R$_7$ as hydrogen, C$_{1-5}$ alkyl, chlorine or bromine;

B and D are together a direct bond;

R$_2$ means hydrogen or an organic acid radical with 1–15 C atoms;

R$_5$ and R$_6$ have the above-indicated meanings;

R$_3$ is a hydrogen atom, C$_{1-10}$ alkyl, cycloalkyl with 5–6 C atoms, a phenyl radical optionally substituted by 1–2 chlorine, bromine, phenyl, C$_{1-4}$ alkyl, C1-4 alkoxy, chloromethyl, fluoromethyl, trifluoromethyl, carboxy or hydroxy, and if R$_4$ means a hydrogen, their salts with physiologically compatible bases and cyclodextrin clathrates.

Especially preferred compounds of this invention are compounds of general formula I, whereby the radicals have the following meaning:

R$_1$ is CH$_2$OH, CONR$_5$R$_6$, COOR$_4$ with R$_4$ meaning a hydrogen atom, an alkyl radical with 1–4 C atoms, R$_2$ means hydrogen or an organic acid radical with 1–6 C atoms, R$_3$ is a hydrogen atom or C$_{1-10}$ alkyl;

R$_5$ and R$_6$ have the above-indicated meanings;

A is a trans, trans—CH=CH—CH=CH or tetramethylene group;

B is a straight-chain or branched-chain alkylene group with up to 5 C atoms;

D is a direct bond or a —C≡C group or a —CH=CR$_7$ group with R$_7$ as hydrogen or C$_{1-5}$ alkyl;

B and D are together a direct bond;

and if R$_4$ means a hydrogen atom, their salts with physiologically compatible bases and their cyclodextrin clathrates.

In addition, the invention relates to a process for the production of the compounds of general formula I according to the invention, which is characterized in that an alcohol of formula II or an intermediate sulfonic acid ester,

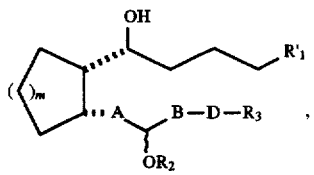

(II)

in which A, B, D, R$_1$, R$_2$ and R$_3$ have the above-indicated meaning and R'$_1$ has the same meaning as R$_1$ or represents grouping —CH$_2$OR$_9$, in which R$_9$ means a readily cleavable ether radical, optionally under protection of free hydroxy groups in OR$_2$, is reacted with a dehydrating reagent or fluorinating reagent of general formula III,

 (III)

in which Alk represents —CH$_3$ or —CH$_2$CH$_3$, optionally in the presence of a base and optionally then separated in any sequence of isomers, protected hydroxy groups are released and/or a free hydroxy group is esterified and/or the 1-hydroxy group is oxidized to carboxylic acid and/or double bonds are hydrogenated and/or an esterified carboxyl group is saponified and/or reduced or a carboxyl group is esterified and/or a free carboxyl group is converted to an amide or a carboxyl group is converted to a salt with a physiologically compatible base.

As ether radicals R$_9$ in the compound of formula II, the radicals that are familiar to one skilled in the art are considered. Preferred are readily cleavable ether radicals, such as, for example, dimethyl-tert-butylsilyl, trimethylsilyl, tribenzylsilyl, diphenyl-tert-butylsilyl, tetrahydropyranyl, tetrahydrofuranyl and α-ethoxyethyl, to name only a few.

The reaction of the compound of general formula II with a fluorinating reagent of general formula III is performed at temperatures of –100° C. to 100° C., preferably –78° C. to 80° C. in an aprotic solvent or solvent mixture, for example, tetrahydrofuran, diethyl ether, optionally in the presence of an amine. As amines, for example, triethylamine, dimethylaminopyridine or pyridine are suitable. In this reaction, in addition to the 5-fluorine compound, the Δ$^{5,6}$-olefin, which can be separated by chromatography, is also obtained.

If it is desired to obtain only the Δ$^{5,6}$-olefin, the hydroxy group can be cleaved optionally with an intermediate sulfonic acid ester. As a dehydrating reagent, for example, the so-called Burgess reagent (J. Am. Chem. Soc. 90, 4744 (1968)) is suitable.

The reaction of the compound of general formula II to an intermediate 9-sulfonic acid ester is carried out in a way known in the art with an alkyl or aryl sulfonyl chloride or alkyl or arylsulfonyl anhydride in the presence of an amine, such as, for example, pyridine, triethylamine or DMAP at temperatures between –60° C. and +100° C., preferably –20° C. to +50° C. The elimination of the 5-sulfonate is carried out with a base, preferably potassium-tert-butylate, 1, 5-diazabicyclo[4.3.0]-non-5-ene or 1, 8-diazabicyclo[5.4.0]undec-7-ene in an inert solvent, such as, for example, dimethylformamide, dimethylacetamide, dimethyl sulfoxide, dimethoxyethane, tetrahydrofuran, etc., at temperatures between 0° C. and 100° C., preferably 20° C. to 80° C.

The reduction to the compounds of formula I with R$_1$ meaning a CH$_2$OH group is performed with a reducing agent that is suitable for the reduction of esters or carboxylic acids, such as, for example, lithium aluminum hydride, diisobutyl aluminum hydride, etc. As a solvent, diethyl ether, tetrahydrofuran, dimethoxyethane, toluene, etc. are suitable. The reduction is performed at temperatures of –30° C. up to boiling temperature of the solvent used, preferably 0° C. to 30° C.

The esterification of the alcohols of formula I (R$_2$=H) is carried out in a way known in the art. For example, the esterification is carried out in that an acid derivative, preferably an acid halide or acid anhydride, is reacted with an alcohol of formula I in the presence of a base such as, for example, NaH, pyridine, triethylamine, tributylamine or 4-dimethylaminopyridine. The reaction can be performed without a solvent or in an inert solvent, preferably acetone, acetonitrile, dimethylacetamide, dimethyl sulfoxide at temperatures above or below room temperature, for example, between –80° C. to 100° C., preferably at room temperature.

The oxidation of the 1-hydroxy group is performed according to methods that are known to one skilled in the art. As oxidizing agents, for example, there can be used: pyridinium dichromate (Tetrahedron Letters, 1979, 399), Jones reagent (J. Chem. Soc. 1953, 2555) or platinum/oxygen (Adv. in Carbohydrate Chem. 17, 169 (1962) or Collins oxidation (Tetrahedron Letters 1968, 3363 and subsequent Jones Oxidation. The oxidation with pyridinium dichromate is performed at temperatures of 0° C. to 100° C., preferably at 20° C. to 40° C. in a solvent that is inert with respect to the oxidizing agent, for example, dimethylformamide.

The oxidation with Jones reagent is carried out at temperatures of −40° C. to +40° C., preferably 0° C. to 30° C., in acetone as a solvent.

The oxidation with platinum/oxygen is performed at temperatures of 0° C. to 60° C., preferably 20° C. to 40° C., in a solvent that is inert with respect to the oxidizing agent, such as, e.g., ethyl acetate.

The saponification of the esters of formula I is performed according to the methods known to one skilled in the art, such as, for example, with basic catalysts. The compounds of formula I can be separated by the conventional separating methods into optical isomers (Asymmetric Synthesis, Vol. 1–5, Ed. J. D. Morrison, Academic Press, Inc., Orlando etc., 1985; Chiral Separations by HPLC, Ed. A. M. Krstulovic; John Wiley & Sons; New York etc. 1989).

The release of the functionally modified hydroxy groups is carried out according to known methods. For example, the cleavage of hydroxy protective groups, such as, for example, the tetrahydropyranyl radical, is performed in an aqueous solution of an organic acid, such as, e.g., oxalic acid, acetic acid, propionic acid, i.a., or in an aqueous solution of an inorganic acid, such as, e.g., hydrochloric acid. To improve the solubility, a water-miscible inert organic solvent is suitably added. Suitable organic solvents are, e.g., alcohols, such as methol and ethanol, and ethers, such as dimethoxyethane, dioxane and tetrahydrofuran. Tetrahydrofuran is preferably used. The cleavage is performed preferably at temperatures between 20° C. and 80° C. The cleavage of the silyl ether protective groups is carried out, for example, with tetrabutylammonium fluoride or with potassium fluoride in the presence of a crown ether (such as, for example, dibenzo[18]-crown-6). As a solvent, for example, tetrahydrofuran, diethyl ether, dioxane, dichloromethane, etc., are suitable. The cleavage is performed preferably at temperatures between 0° C. and 80° C.

The saponification of the acyl groups is carried out, for example, with alkali or alkaline-earth carbonates or -hydroxides in an alcohol or in the aqueous solution of an alcohol. As an alcohol, lower aliphatic alcohols, such as, e.g., methanol, ethanol, butanol, etc., preferably methanol, are considered. As alkali carbonates and -hydroxides, potassium and sodium salts can be mentioned. Preferred are potassium salts.

As alkaline-earth carbonates and -hydroxides, for example, calcium carbonate, calcium hydroxide and barium carbonate are suitable. The reaction is carried out at −10° C. to +70° C., preferably at +25° C.

The introduction of ester group —COOR$_4$ for R$_1$, in which R$_4$ represents an alkyl group with 1–10 C atoms, is carried out according to the methods known to one skilled in the art. The 1-carboxy compounds are reacted, for example, with diazohydrocarbons in a way known in the art. The esterification with diazohydrocarbons is carried out, e.g., in that a solution of the diazohydrocarbon in an inert solvent, preferably in diethyl ether, is mixed with the 1-carboxy compound in the same solvent or in another inert solvent, such as, e.g., methylene chloride. After the reaction is completed in 1 to 30 minutes, the solvent is removed, and the ester is purified in the usual way. Diazoalkanes are either known or can be produced according to known methods [Org. Reactions Vol. 8, pages 389–394 (1954)].

The introduction of ester group —COOR$_4$ for R$_1$, in which R$_4$ represents a substituted or unsubstituted aryl group, is carried out according to the methods known to one skilled in the art. For example, the 1-carboxy compounds are reacted in an inert solvent with the corresponding arylhydroxy compounds with dicyclohexylcarbodiimide in the presence of a suitable base, for example, pyridine, dimethylaminopyridine, triethylamine. As a solvent, methylene chloride, ethylene chloride, chloroform, ethyl acetate, tetrahydrofuran, preferably chloroform, are suitable. The reaction is performed at temperatures between −30° C. and +50° C., preferably at 10° C.

If C=C double bonds that are contained in the primary product are to be reduced, the hydrogenation is carried out according to methods known in the art.

The hydrogenation of the $\Delta^{8,10}$-diene system is performed in a way known in the art at low temperatures, preferably at about −20° C. to +30° C. in a hydrogen atmosphere in the presence of a noble metal catalyst. As a catalyst, for example, 10% palladium on carbon is suitable.

The leukotriene-B$_4$ derivatives of formula I with R$_4$ meaning a hydrogen can be converted to a salt with suitable amounts of the corresponding inorganic bases with neutralization. For example, in dissolving the corresponding acids in water, which contains the stoichiometric amount of the base, the solid inorganic salt is obtained after water is evaporated or after a water-miscible solvent, e.g., alcohol or acetone, is added.

For the production of an amine salt, LTB$_4$ acid is dissolved in, e.g., a suitable solvent, for example, ethanol, acetone, diethyl ether, acetonitrile or benzene, and at least the stoichiometric amount of the amine is added to the solution. In this way, the salt usually accumulates in solid form or is isolated after the solvent is evaporated in the usual way.

The introduction of amide group —CONHR$_5$ with R$_5$, meaning alkanoyl is carried out according to the methods known to one skilled in the art. The carboxylic acids of formula I (R$_4$=H) are first converted to the mixed anhydride in the presence of a tertiary amine, such as, for example, triethylamine, with chloroformic acid butyl ester. The reaction of the mixed anhydride with the alkali salt of the corresponding amide or with ammonia (R$_5$=H) is carried out in an inert solvent or solvent mixture, such as, for example, tetrahydrofuran, dimethoxyethane, dimethylformamide, hexamethylphosphoric acid triamide, at temperatures between −30° C. and +60° C., preferably at 0° C. to 30° C. Another type of production of the amides involves the amidolysis of 1-ester (R$_1$=COOR$_4$) with the corresponding amine.

Another possibility for the introduction of amide group —CONHR$_5$ involves the reaction of a 1-carboxylic acid of formula I (R$_4$=H), in which free hydroxy groups are optionally intermediately protected, with compounds of formula IV, $$O=C=N-R_5 \qquad (IV)$$

in which R$_5$ has the above-indicated meaning.

The reaction of the compound of formula I (R$_4$=H) with an isocyanate of formula IV is carried out optionally with the addition of a tertiary amine, such as, e.g., triethylamine or pyridine. The reaction can be performed without a solvent or in an inert solvent, preferably acetonitrile, tetrahydrofuran, acetone, dimethylacetamide, methylene chloride, diethyl ether, toluene, at temperatures between −80° C. to 100° C., preferably at 0° C. to 30° C.

For the production of the other amides, for example, the desired acid anhydride can be reacted with ammonia or the corresponding amines.

If the starting product contains OH groups in the leukotriene-B$_4$ radical, these OH groups are also brought to reaction. If end products that contain free hydroxyl groups are ultimately desired, a start is suitably made from starting products in which the latter are intermediately protected by preferably readily cleavable ether or acyl radicals.

The separation of the diastereomers is carried out according to methods known to one skilled in the art, for example by column chromatography.

The compounds of formula II that are used as starting material are described in DE-A 42 27 790.6 or can be produced, for example, by cis-1, 2-diacetoxymethyl-cyclohex-4-ene or cis-1, 2-diacetoxymethyl-cyclohexane or cis-1, 2-diacetoxymethyl cyclopentane or cis-1, 2-diacetoxymethylcycloheptane being enantioselectively hydrolyzed with a lipase in a way known in the art (J. B. Jones et al., J. Chem. Soc. Chem. Commun. 1985, 1563; M. Schneider et al., Tetrahedron Lett. 26, 2073 (1985); H. J. Gais et al., Tetrahedron Lett. 28, 3471 (1987)). The optically active monoacetate that is produced in this way is then converted to the tert-butyldimethylsilyl ether, optionally hydrogenated and then converted with diisobutyl aluminum hydride to the monosilyl ether of formula V

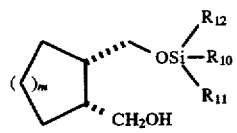

in which $R_{10}$, $R_{11}$ and $R_{12}$ are the same or different and mean $C_1$-$C_4$ alkyl or phenyl.

By the oxidation, e.g., with Collins reagent or by the Swern process (Tetrahedron Letters 34, 1651 (1978)), the aldehyde of formula VI is obtained

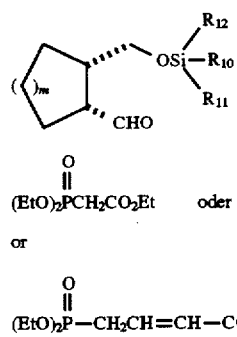

which is converted in a Wittig-Horner olefination with the phosphonate of formula VII and a base and optionally subsequent hydrogenation as well as subsequent reduction of the ester group, oxidation of the primary alcohol, repeated Wittig-Horner olefination with the phosphonate of formula VII and optionally subsequent hydrogenation to the ester of formula IX or a Wittig-Horner reaction of the aldehyde of formula VI with a phosphonate of formula VIII, whereby A

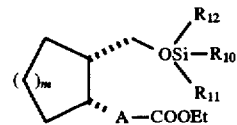

has the above-indicated meaning. As bases, for example, potassium tert-butylate, diazabicyclononane, diazabicycloundecane or sodium hydride are suitable. Reduction of the ester group, for example with diisobutyl aluminum hydride, and subsequent oxidation of the primary alcohol obtained, e.g., with manganese dioxide or Collins reagent, results in an aldehyde of formula X

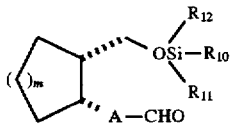

The organometallic reaction of the aldehyde of formula X with a Grignard reagent of formula XI, in which B, D

and $R_3$ have the above-indicated meanings and X means chlorine, bromine or iodine, results, under protection of the hydroxy groups (for example by acylation) and optionally diastereomer separation, in the compounds of formula XII

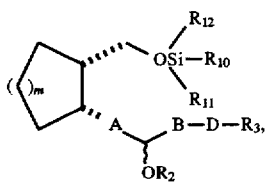

The production of the compound of formula XI that is required for the organometallic reaction is carried out by reaction of the corresponding terminal halide with magnesium. By reaction of silyl ether XII with tetrabutylammonium fluoride and optionally diastereomer separation, the alcohol of formula XIII is obtained.

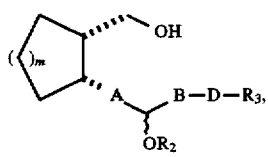

The compounds of formula XII, in which B means a CH$_2$ group and D means a —C≡C— group or a CH=CR$_7$ group, can be obtained, for example, by an organometallic reaction of a propargyl halide and subsequent alkylation with a corresponding alkyl halide and optionally subsequent Lindlar hydrogenation.

An alternative structure of the lower chain starts from the aldehyde of formula XIV, which resulted from the Wittig-Horner reaction of aldehyde VI and subsequent reduction and oxidation.

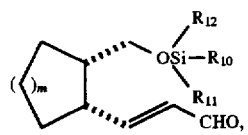

Wittig-Horner olefination of aldehyde XIII with a phosphonate of formula XV

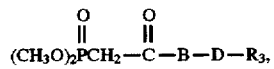

and reduction of the ketone that is produced then resulted in an alcohol of formula XII and, after acylation and silyl ether cleavage, in an alcohol of formula III, which optionally can be separated into diastereomers.

The compounds of general formula XIII are described in DE-A 42 27 790.6 or can be produced according to the process that is presented in DE-A 42 27 790.6.

The oxidation of the primary alcohol group in XIII, e.g., with Collins reagent or pyridinium dichromate or with the Swern method results in an aldehyde of formula XVI

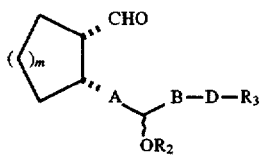 (XVI)

The reaction of the aldehyde of general formula XVI with a magnesium-organic compound of formula

 (XVII)

in which Hal represents chlorine, bromine or iodine, and $R'_1$ represents —$CH_3$, $CF_3$ or —$CH_2OR_9$, in which $R_9$ means a readily cleavable ether radical, results in an alcohol of general formula II. Then, isomers can be separated optionally in any sequence, protected hydroxy groups can be released and/or a free hydroxy group oxidized to carboxylic acid and/or double bonds hydrogenated and/or an esterified carboxyl group ($R_1$=COOR$_5$) saponified and/or a carboxyl group ($R_5$=H) esterified and/or a free carboxyl group ($R_5$=H) converted to an amide ($R_1$=CONR$_6$R$_7$) or a carboxyl group converted to a salt with a physiologically compatible base.

As ether radicals $R_9$ in the compound of formula II, the radicals that are familiar to one skilled in the art are considered. Preferred are readily cleavable ether radicals, such as, for example, dimethyl-tert-butylsilyl, trimethylsilyl, tribenzylsilyl, diphenyl-tert-butylsilyl, tetrahydropyranyl, tetrahydrofuranyl and α-ethoxyethyl, to name only a few.

The reaction of the compound of formula II with an organometallic compound of formula XVII is carried out in a way known in the art in an inert solvent or solvent mixture, such as, for example, dioxane, toluene, dimethoxyethane or preferably diethyl ether or tetrahydrofuran. The reaction is performed at temperatures between −100° C. and 60° C., preferably at 78° C. to 0° C.

The production of compound XVII that is required for this reaction is carried out by reaction of the corresponding hydroxy halide that is protected by a readily cleavable ether group and subsequent reaction with magnesium.

The incorporation of the chemically and metabolically labile cis-$\Delta^{6,7}$ double bond of LTB$_4$ into a cis-1, 2-substituted cycloalkyl ring results in a stabilization, whereby especially by further derivatization of the functional groups and/or structural changes of the lower side chain, LTB$_4$ derivatives that can act as LTB$_4$ antagonists were obtained (DE-A 39 17 597 and DE-A 42 27 790.6 and DE-A 41 08 351 and 41 39 886.8).

It has now been found that by substitution of the 5-hydroxy group by a fluorine atom or by introduction of a double bond in 5, 6-position (numbering system beginning with a carboxy-C atom with 1) and omission of the hydroxy group in 5-position in such leukotriene-B$_4$ derivatives, a prolonged duration of action, greater selectivity and better effectiveness can be achieved.

The compounds of formula I act in an antiinflammatory, antiallergic and antiproliferative manner. In addition, they have antimycotic properties. Consequently, the new leukotriene-B$_4$ derivatives of formula I represent valuable pharmaceutical active ingredients. The compounds of formula I are especially suitable for topical administration, since they exhibit a dissociation between desired topical effectiveness and undesirable systemic side effects.

The new leukotriene-B$_4$ derivatives of formula I are suitable in combination with the additives and vehicles that are commonly used in galenic pharmaceutics for topical treatment of diseases of the skin, in which leukotrienes play an important role, e.g.: contact dermatitis, eczemas of the most varied types, neurodermatoses, erythrodermia, pruritus vulvae et ani, rosacea, cutaneus lupus erythematosus, psoriasis, lichen ruber planus et verrucosis and similar skin diseases.

In addition, the new leukotriene-B$_4$ antagonists are suitable for the treatment of multiple sclerosis and symptoms of shock.

The production of the pharmaceutical agent specialties is carried out in the usual way by the active ingredients being converted with suitable additives to the desired form of administration, such as, for example: solutions, ointments, creams or patches.

In the thus formulated pharmaceutical agents, the active ingredient concentration depends on the form of administration. In lotions and ointments, an active ingredient concentration of 0.0001% to 3% is preferably used.

Further, the new compounds optionally in combination with the usual vehicles and adjuvants are also well-suited for the production of inhalants, which can be used to treat allergic diseases of the respiratory system, such as, for example, bronchial asthma or rhinitis.

Further, the new leukotriene-B$_4$ derivatives are also suitable in the form of capsules, tablets or coated tablets, which preferably contain 0.1 to 100 mg of active ingredient and are administered orally or in the form of suspensions, which preferably contain 1–200 mg of active ingredient per dosage unit, and are also administered rectally to treat diseases of the internal organs, in which leukotrienes play an important role, such as, e.g.: allergic diseases of the intestinal tract, such as colitis ulcerosa and colitis granulomatosa.

In these new forms of administration, the new LTB$_4$ derivatives, in addition to the treatment of diseases of internal organs with inflammatory processes, are also suitable for the treatment of diseases in which, leukotriene-dependent, the increased growth and the new formation of cells are important. Examples are leukemia (increased growth of white blood cells) or arteriosclerosis (increased growth of unstriped muscle cells of blood vessels).

The new leukotriene-B$_4$ derivatives can also be used in combination, such as, e.g., with lipoxygenase inhibitors, cyclooxygenase inhibitors, glucocorticoids, prostacyclin agonists, thromboxane antagonists, leukotriene-D$_4$ antagonists, leukotriene-E$_4$ antagonists, leukotriene-F$_4$ antagonists, phosphodiesterase inhibitors, calcium antagonists, PAF antagonists or other known forms of treatment of the respective diseases.

The following embodiments are used for a more detailed explanation of the process according to the invention. In the examples, diastereomers in 12-position that are not characterized in more detail were characterized as polar or nonpolar (e.g., diastereomer unpol (12)).

EXAMPLE 1

5-[(E)-(2S)-2-((1E, 3E)-(5S)-5-Hydroxy-6, 6-trimethylene-9-phenyl-1, 3-nonadien-8-inyl)-cyclohexylidene]-pentanoic acid diastereomer pol (12)

0.39 ml of diethylamino sulfur trifluoride is added in drops to a solution of 1.82 g of (5S)-5-hydroxy-5-[cis-(2S)-2-((1E, 3E)-(5S)-5-acetoxy-6, 6-trimethylene-9-phenyl-1, 3-nonadien-8-inyl)-(1S)-cyclohexyl]-pentan-1-ol-tert-butyldimethylsilyl ether (diastereomer pol (12)) in 28 ml of dichloromethane and 0.78 ml of pyridine at −70° C. under argon, and it is stirred for 2 hours at −70° C. It is allowed to heat to room temperature, a 5% sodium bicarbonate solution is carefully added, stirred for 15 minutes, diluted with 200 ml of dichloromethane and washed with 30 ml of brine each. It is dried on sodium sulfate and concentrated by evaporation in a vacuum. The residue is separated by chromatography on silica gel. With hexane/ethyl acetate (97+3 and 94+6), first obtained as a nonpolar component is 280 mg of 5-[(E)-(2S)-2-((1E, 3E)-(5S)-5-acetoxy-6, 6-trimethylene-9-phenyl-1, 3-nonadien-8-inyl-cyclohexylidene]-pentan-1-ol-tert-butyldimethylsilyl ether, 800 mg of mixed fractions, and obtained as a polar component is 550 mg of (5R)-5-fluoro-5-[cis-(2S)-2-((1E, 3E)-(5S)-5-acetoxy-6, 6-trimethylene-9-phenyl-1, 3-nonadien-8-inyl-(1S)-cyclohexyl]-pentan-1-ol-tert-butyldimethylsilyl ether as a colorless oil.

IR spectrum of the olefin: $(CHCl_3)$ 2930, 2858, 1729, 1248, 990, 837 $cm^{-1}$.

For silyl ether cleavage, 220 m g of the nonpolar olefin, produced above, in 12 ml of tetrahydrofuran is stirred with 363 mg of tetrabutylammonium fluoride for 3 hours at 24° C. under argon. Then, it is diluted with diethyl ether, washed three times with water, dried on sodium sulfate and concentrated by evaporation in a vacuum. The residue is chromatographed with hexane/ethyl acetate (8+2) on silica gel. In this case, 140 mg of 1-alcohol is obtained as a colorless oil (polar component). As a nonpolar component, 50 mg of the Z-configured $\Delta^{5,6}$-olefin is separated here.

IR: 3430, 2925, 2850, 2220, 1735, 1665, 1240, 992 $cm^{-1}$.

For oxidation of the 1-hydroxy group, 1.6 g of Collins reagent (bis-pyridine-chromium(VI) oxide complex; Tetrahedron Letters 1968, 3363) is added at 0° C. to 350 mg of the alcohol, produced above, in 25 ml of dichloromethane, and it is stirred for, 10 minutes at 0° C. Then, it is diluted with a mixture of hexane/diethyl ether (1+1), Celite is added, filtered, washed with hexane/diethyl ether (1+1) and concentrated by evaporation in a vacuum. The thus obtained 1-aldehyde is used immediately without further purification.

0.52 ml of Jones reagent (chromium(VI) oxide in $H_2SO_4$; J. Chem. Soc. 1953, 2555) is added in drops to a solution of 320 mg of the aldehyde, produced above, in 6 ml of acetone while being stirred at −20° C., and it is stirred for 10 minutes at −20° C. under argon. Then, 2.5 ml of isopropanol is added, it is stirred for 5 minutes, diluted with 50 ml of diethyl ether, shaken twice with brine, dried on sodium sulfate and concentrated by evaporation in a vacuum. The residue is chromatographed on silica gel. With hexane/ethyl acetate (3+2), 260 mg of the 1-carboxylic acid is obtained as a colorless oil.

IR: 3520, 2935, 2860, 1728, 1245, 992 $cm^{-1}$.

For acetate saponification, 5.3 ml of a 0.5N sodium hydroxide solution is added to 250 mg of the acid, produced above, in 5 ml of methanol at 25° C., and it is stirred for 5 hours at 25° C. under argon. Then, it is acidified with 1N sulfuric acid to pH 4–5. It is extracted with ethyl acetate, washed twice with brine, dried on sodium sulfate and concentrated by evaporation in a vacuum. The residue is chromatographed on silica gel. With ethyl acetate, 211 mg of the title compound is obtained as a colorless oil.

IR: 3400, 2930, 2855, 2220, 1708, 1599, 1490, 992 $cm^{-1}$.

The starting material for the above compound is produced as follows:

1a) 2-Oxo-3, 3-trimethylene-6-phenyl-hex-5-ine-phosPhonic acid dimethyl ester 250 ml of a 1.6 molar butyllithium solution in hexane and then a solution of 20 g of cyclobutanecarboxylic acid in 20 ml of tetrahydrofuran are added to a solution of 4.1 g of diisopropylamine in 180 ml of tetrahydrofuran at −30° C. It is stirred for another 40 minutes at −10° C., and then 43 g of 1-bromo- 3-phenyl-2-propine is added in drops, stirred for 16 hours at 25° C. and poured onto 400 ml of ice water. After acidification with 2N hydrochloric acid to pH 4, it is extracted with diethyl ether, the extract is washed with brine, dried on magnesium sulfate and concentrated by evaporation in a vacuum. The residue is dissolved in 83 ml of methanol, mixed with 4.3 ml of concentrated sulfuric acid and refluxed for 6 hours. It is cooled, ice water is stirred in and extracted with diethyl ether. The extract is washed neutral with water, dried with sodium sulfate, and the diethyl ether is concentrated by evaporation in a vacuum. After distillation (boiling point 123°–125° C. at 0.05 mm), 43 g of 2, 2-trimethylene-5-phenyl-pent-4-inoic acid methyl ester is obtained.

268 ml of 1.6 M butyllithium solution in hexane is added in drops to a solution of 59 g of methanephosphonic acid dimethyl ester in 700 ml of tetrahydrofuran at −70° C. After 1 hour, a solution of 44 g of the ester, produced above, in 120 ml of tetrahydrofuran is added in drops and stirred for another 5 hours at −70° C. Then, it is mixed with 35 ml of ethyl acetate and concentrated by evaporation in a vacuum. The residue is dissolved in 100 ml of water and extracted three times with 400 ml of dichloromethane each. It is dried on sodium sulfate and concentrated by evaporation in a vacuum. The residue is purified by column chromatography on silica gel. With ethyl acetate, 43 g of the phosphonate is obtained as a colorless liquid.

IR: 3420, 2998, 2875, 1703, 1250 $cm^{-1}$.

1b) cis-(1S)-1-(Tert-butyl-dimethylsilyloxy-methyl)-2(R)-2-formyl-cyclohexane 481 g of imidazole and 532 g of tert-butyldimethylsilyl chloride are added to a solution of 500 g of cis-(1S)-hydroxymethyl-(2R)-acetoxymethyl-cyclohex-4-ene (produced, for example, according to K. Laumen et al., Tetrahedron Letters 26, 2073 (1985)) in 2400 ml of dimethylformamide at 0° C., and it is stirred for 20 hours at 24° C. It is diluted with diethyl ether, shaken with 500 ml of a 5% sulfuric acid, washed neutral with brine, dried on magnesium sulfate and concentrated by evaporation in a vacuum. The residue is chromatographed on silica gel. With hexane/ethyl acetate mixtures, 519 g of cis-(1S)-tert-butyl-dimethylsilyloxymethyl-(2R)-acetoxymethyl-cyclohex-4-ene is obtained.

For hydrogenation, 379 g of the silyl ether, produced above, in 2.400 ml of ethyl acetate is stirred with 20 g of palladium-10% on carbon under a hydrogen atmosphere at room temperature and normal pressure. After 6 hours, no hydrogen absorption could be detected. The reaction mixture was filtered and concentrated by evaporation in a vacuum. In this case, 359 g of the hydrogenated compound was obtained.

$[\alpha]_D$=−7.1°(c=1.005, acetone)

For acetate cleavage, 194 ml of an approximately 1.2 molar solution of diisobutyl aluminum hydride in toluene is added in drops to a solution of 35 g of the silyl ether, produced above, in 450 ml of toluene, and it is stirred for 15 minutes at −70° C. Subsequently, 80 ml of isopropanol and then 97 ml of water are added in drops, stirred for 2 hours at 22° C., filtered, washed with toluene and concentrated by evaporation in a vacuum. The residue is purified by chromatography on silica gel. With hexane/ethyl acetate (9+1), 22 g of the alcohol is obtained as a colorless oil.

$[\alpha]_D$=+3.5°(c=1.350/acetone); IR: 3420, 2925, 2858, 1465, 1255, 833 $cm^{-1}$.

For conversion of the hydroxy group to the formyl group, 15.9 g of dimethyl sulfoxide in 60 ml of dichloromethane is added in drops at −70° C. to a solution of 12 g of oxalyl chloride in 90 ml of dichloromethane, and it is stirred for 10 minutes at −60° C. A solution of 19.5 g of the alcohol, produced above, in 60 ml of dichloromethane is added to this solution at −60° C., it is stirred for 1.5 hours at −60° C., 30 ml of triethylamine is added in drops and stirred for 1.5 hours at −50° C. Then, it is poured into 100 ml of ice water, extracted twice with 50 ml of dichloromethane each, washed with water, shaken once with 50 ml of 5% citric acid and washed twice with brine. It is dried on sodium sulfate and concentrated by evaporation in a vacuum. 19.2 g of the aldehyde, which is used without further purification, is obtained.

IR: 2930, 2858, 2730, 1713, 840 cm$^{-1}$. 1c) 3-[cis-(1S)-1-Tert-butyl-dimethylsilyloxymethyl]-(2S)-cyclohex-2-yl]-(2E) -propen-1-al 20.7 ml of phosphonoacetic acid triethyl ester and then 13.9 ml of diazabicycloundecene (DBU) are added in drops to a suspension of 4.42 g of lithium chloride in 300 ml of acetonitrile under argon at room temperature, and it is stirred for 15 minutes. Then, a solution of 19.12 g of the aldehyde, produced under 1b, in 40 ml of acetonitrile is added in drops, stirred for 3 hours at 24° C. and then diluted with diethyl ether. It is shaken in succession with water, 10% sulfuric acid and water, dried with sodium sulfate and concentrated by evaporation in a vacuum. The residue is chromatographed with hexane/diethyl ether (9+1) on silica gel. In this case, 17 g of the α, β-unsaturated ester is obtained as a colorless oil.

IR: 2930, 2838, 1706, 1648, 1270, 840 cm$^{-1}$.

To reduce the ester group, 86 ml of a 1.2 molar solution of dsobutyl aluminum hydride in toluene is added in drops to a solution of 17 g of the ester, produced above, in 240 ml of toluene at −70° C., and it is stirred for 30 minutes at −70° C. subsequently, 30 ml of isopropanol and then 40 ml of water are added in drops, stirred for 2 hours at 22° C., filter red , washed with dichloromethane and concentrated by evaporation in a vacuum. The residue is chromatographed with hexane/ethyl acetate (4+1) on silica gel. In this case, 14.5 g of the ally alcohol is obtained as a colorless oil.

IR: 3610, 3450, 2930, 2858, 1460, 838 cm$^{-1}$.

A solution of 14.4 g of the alcohol, produced above, in 280 ml of toluene is mixed with 44 g of manganese dioxide, and it is stirred for 5 hours at 24° C. Then, it is filtered, concentrated by evaporation and chromatographed on silica gel. With hexane/diethyl ether (9+1), 13.3 g of the aldehyde is eluted as a colorless oil.

IR: 2930, 2860, 2740, 1685, 1630, 840 cm$^{-1}$.
1d) (5S)-5-Acetoxy-1-[cis-(1S)-1-hydroxymethyl]-(2S)-cyclohex-2-yl]-6, 6-trimethylene-9-phenyl-(1E, 3E)-1, 3-nonadien-8-ine A solution of 40.10 g of 2-oxo-3, 3-trimethylene-6-phenyl-hex-5-ine-phosphonic acid dimethyl ester in 290 ml of dimethoxyethane is added in drops to a suspension of 5 g of sodium hydride (60% suspension in oil) in 190 ml of dimethoxyethane at 0° C., and it is stirred for 1 hour at 0° C. Then, a solution of the aldehyde (30.75 g), described under 1c), in 350 ml of dimethoxyethane is added in drops, stirred for 1 hour at 0° C., 4 hours at 25° C. and then poured onto 200 ml of saturated ammonium chloride solution. It is extracted three times with diethyl ether, the organic phase is washed with water, dried on magnesium sulfate and concentrated by evaporation in a vacuum. The residue is purified by column chromatography on silica gel. With hexane/diethyl ether (9+1), 41 g of the α, β-unsaturated ketone is obtained as a colorless oil.

IR: 2925, 2858, 1673, 1625, 1590, 1001, 838 cm$^{-1}$.

To reduce the keto group, 4.75 g of Ce(III) chloride heptahydrate is added to a solution of 40.5 g of the ketone, described above, in 700 ml of methanol and 74 ml of tetrahydrofuran at −60° C., it is stirred for 20 minutes and then mixed in portions with 5 g of sodium borohydride. It is stirred for 20 minutes at −60° C., mixed with 34 ml of acetone, stirred for 15 minutes, neutralized at room temperature with glacial acetic acid and concentrated by evaporation in a vacuum. Then, the residue is taken up in a diethyl ether/water mixture, the aqueous phase is shaken with diethyl ether, the organic phase is washed neutral with water, dried on sodium sulfate and concentrated by evaporation in a vacuum. The residue is chromatographed several times on silica gel columns. With hexane/ethyl acetate (8+2), first 11 g of the nonpolar R-configured alcohol (5R)-5-hydroxy-1-[cis-(1S)-1-(tert-butyl-dimethylsilyloxymethyl)-(2S)-cyclohex-2-yl]-6, 6-trimethylene-9-phenyl-(1E, 3E)-1, 3-nonadien-8-ine as well as 18 g of the polar S-configured alcohol (5S)-5-hydroxy-1-[cis-(1S)-1-tert-butyldimethylsilyloxymethyl)-(2S)-cyclohex-2-yl]-6, 6-trimethylene-9-phenyl-(1E, 3E)-1, 3-nonadien-8-ine are obtained as colorless oils.

IR (polar alcohol): 3530, 2925, 2853, 990, 838 cm$^{-1}$.

For acetylation, 30 ml of acetic anhydride is added to a solution of 17.8 g of the polar alcohol, produced above, in 60 ml of pyridine, and it is stirred for 16 hours at room temperature. Then, it is concentrated by evaporation in a vacuum with the addition of toluene, and the residue is chromatographed on silica gel. With hexane/diethyl ether (9+1), 19.1 g of the acetate is obtained as a colorless oil.

IR: 2925, 2852, 1727, 1245, 990, 838 cm$^{-1}$.

For silyl ether cleavage, 25 g of tetrabutylammonium fluoride is added to 19.1 g of the acetate, produced above, in 480 ml of tetrahydrofuran at 0° C., and it is stirred for 3 hours at 24° C. Then, it is diluted with diethyl ether and washed three times with brine. It is dried on magnesium sulfate, concentrated by evaporation in a vacuum, and the residue is chromatographed on silica gel. With hexane/ethyl acetate (7+3), 14 g of the alcohol is eluted as a colorless oil.

IR: 3450, 2930, 2858, 1729, 1245, 990 cm$^{-1}$.

1e) (5S)-5-Hydroxy-5-[cis-(2S)-2-((1E, 3E)-(5S)-5-acetoxy-6, 6-trimethylene-9-phenyl-1, 3-nonadien-8-inyl)-(1S)-cyclohexyl]-pentan-1-ol-tert-butyldimethylsilyl ether diastereomer pol (12)

45 g of Collins reagent (chromic acid-pyridine complex) is added to a solution of 8.95 g of the alcohol, produced above under 1d), in 230 ml of dichloromethane at 0° C., and it is stirred for 15 minutes at 0° C. Then, it is diluted with a mixture of hexane/diethyl ether (2+1), Celite is added, filtered and concentrated by evaporation in a vacuum. The thus obtained aldehyde was used without further purification (raw yield 8.2 g).

IR: 2930, 2858, 2720, 1723, 1245, 990, 968 cm$^{-1}$.

For Grignard reaction, a solution of 26.7 g of 4-chloro-1-(tert-butyldimethylsilyloxy)-butane in 24 ml of tetrahydrofuran is added in drops to 5.76 g of magnesium at 25° C. under argon, a crystal of iodine was added and stirred for 30 minutes at 60° C. Then, it is diluted with 74 ml of tetrahydrofuran.

The solution of 4.6 g of the aldehyde, produced above, in 35 ml of tetrahydrofuran is added in drops to 23 ml of this Grignard solution under argon at −70° C., and it is stirred for 30 minutes at −70° C. It is mixed with saturated ammonium chloride solution, extracted three times with diethyl ether, the organic phase is shaken with brine, dried on sodium sulfate and concentrated by evaporation in a vacuum. The residue is chromatographed on silica gel. With hexane/ diethyl ether (9+1), first obtained is 720 mg of the 5R-configured diastereomer alcohol and obtained as polar component is 3.6 g of the 5-configured diastereomer alcohol (title compound).

IR: 3580, 2923, 2850, 1728, 1245, 990, 965, 835 cm$^{-1}$.

EXAMPLE 2

(5R)-5-Fluoro-5-[cis-(2S)-2-((1E, 3E)-(5S)-5-hydroxy-6, 6-trimethylene-9-phenyl-1, 3-nonadien-8-inyl)-(1S)-cyclohexyl]-pentanoic acid diastereomer pol (12)

860 mg of tetrabutylammonium fluoride is added to a solution of 540 mg of (5R)-5-fluoro-5-[cis-(2S)-2-((1E, 3E)-(5S)-5-acetoxy-6, 6-trimethylene-9-phenyl-1, 3-nonadien-8-inyl)-(1S)-cyclohexyl]-pentan-1-ol-tert-butyldimethylsilyl ether in 24 ml of tetrahydrofuran, produced in Example 1, and it is stirred for 3 hours at 24° C. under argon. Then, it is diluted with diethyl ether, washed three times with water, dried on sodium sulfate and concentrated by evaporation in a vacuum. The residue is chromatographed with hexane/ethyl acetate (7+3) on silica gel. In this case, 393 mg of 1-alcohol is obtained as a colorless oil.

IR: 3450, 2930, 2860, 1738, 1243, 992 cm$^{-1}$.

For oxidation of the 1-hydroxy group, 2.5 g of Collins reagent is added at 0° C. to 580 mg of the alcohol, produced above, in 30 ml of dichloromethane, and it is stirred for 10 minutes at 0° C. Then, it is diluted with a mixture of hexane/diethyl ether (1+1), Celite is added, filtered, washed with hexane/diethyl ether (1+1) and concentrated by evaporation in a vacuum. The thus obtained 1-aldehyde is used immediately without further purification.

0.87 ml of Jones reagent is added in drops to a solution of 555 mg of the aldehyde, produced above, in 10 ml of acetone while being stirred at −20° C., and it is stirred for 15 minutes at −20° C. under argon. Then, 3.8 ml of isopropanol is added, it is stirred for 5 minutes, diluted with 50 ml of diethyl ether, shaken twice with brine, dried on sodium sulfate and concentrated by evaporation in a vacuum. The residue is chromatographed on silica gel. With hexane/ethyl acetate (4+1), 520 mg of 1-carboxylic acid is obtained as a colorless oil.

IR: 3450, 2930, 2860, 1738, 1708, 1238, 992 cm$^{-1}$.

For acetate saponification, 10 ml of a 0.5N sodium hydroxide solution is added to 500 mg of the acid, produced above, in 10 ml of methanol at 25° C., and it is stirred for 5 hours at 25° C. under argon. Then, it is acidified with 1N sulfuric acid to pH 4–5. It is extracted with ethyl acetate, washed twice with brine, dried on sodium sulfate and concentrated by evaporation in a vacuum. The residue is chromatographed on silica gel. With ethyl acetate/hexane (4+1), 420 mg of the title compound is obtained as a colorless oil.

IR: 3420, 2934, 2862, 2220, 1710, 1599, 993 cm$^{-1}$.

EXAMPLE 3

5-[(E)-(2S)-2-((1E, 3E)-(5R)-5-Hydroxy-6, 6-trimethylene-9-phenyl-1, 3-nonadien-8-inyl)-cyclohexylidenel]-pentanoic acid diastereomer unpol (12)

Analogously to Example 1, the title compound is obtained as a colorless oil from the nonpolar R-configured alcohol (5R)-5-hydroxy-1-[(cis-(1S)-1-(tert-butyldimethylsilyloxymethyl)-(2S)-cyclohex-2-yl]-6, 6-trimethylene-9-phenyl-(1E, 3E)-1, 3-nonadien-8-ine that is obtained after chromatographic separation in Example 1d.

IR: 3420, 2931, 2856, 2221, 1708, 1600, 1490, 991 cm$^{-1}$.

EXAMPLE 4

(5R)-5-Fluoro-5-[cis-(2S)-2-((1E, 3E)-(5R)-5-hydroxy-6, 6-trimethylene-9-phenyl-1, 3-nonadien-8-inyl-(1S)-cyclohexyl]-pentanoic acid diastereomer unpol (12)

Analogously to Example 2, the title compound is obtained as a colorless oil from the (5R)-5-fluoro-5-[cis-(2S)-2-(1E, 3E)-(5R)-5-acetoxy-6, 6-trimethylene-9-phenyl-1, 3-nonadien-8-inyl)-(1S)-cyclohexyl]-pentan-1-ol-tert-butyldimethylsilyl ether that is produced according to Example 1.

IR: 3400, 2935, 2860, 2220, 1710, 1600, 992 cm$^{-1}$.

EXAMPLE 5

5-[(E)-(2S)-2-((1E, 3E)-(5R)-5-Hydroxy-5-cyclohexyl-1, 3-pentadienyl)-cyclohexylidenel]-pentanoic acid diastereomer pol (12)

Analogously to Example 1, 470 mg of 5-[(E)-(2S)-2-((1E, 3E)-(5R)-5-acetoxy-cyclohexyl-1, 3-pentadienyl)-cyclohexylidene]-pentan-1-ol-tert-butyldimethylsilyl ether, 350 mg of mixed fractions, is obtained as a nonpolar component from 1.5 g of (5S)-5-hydroxy-5-[cis-(2S)-2-((1E, 3E)-(5R)-5-acetoxy-5-cyclohexyl-1, 3-pentadiene)-(1S)]-cyclohexyl)-pentan-1-ol-tert-butyldimethylsilyl ether (diastereomer pol (12)), and as a polar component, 560 mg of (5R)-5-fluoro-5-[cis-(2S)-2-((1E, 3E)-(5R)-5-acetoxy-cyclohexyl-1, 3-pentadienyl)-cyclohexyliden]pentan-1-ol-tert-butyldimethylsilyl ether is obtained as colorless oils.

IR spectrum of the olefin: 2930, 2858, 1735, 1653, 1235, 1100, 990, 836 cm$^{-1}$.

IR spectrum of the fluorine product: 2930, 2858, 1737, 1238, 1102, 990, 938 cm$^{-1}$.

Analogously to the silyl ether cleavage that is described in Example 1, 270 mg of 1-alcohol is obtained as a colorless oil from 460 mg of the olefin, produced above. In addition, 60 mg of the isomeric Z-configured $\Delta^{5,6}$-olefin is separated here.

IR: 3450, 2923, 2858, 1733, 1236, 990, 972 cm$^{-1}$.

Analogously to the oxidation of the 1-hydroxy group that is described in Example 1, 140 mg of 1-carboxylic acid is obtained as a colorless oil from 270 mg of 1-alcohol, produced above.

IR: 3500, 2936, 2860, 1726, 1245, 991 cm$^{-1}$.

Analogously to the acetate saponification described in Example 1, 118 mg of the title compound is obtained as a colorless oil from 140 mg of carboxylic acid, produced above.

IR: 3400, 2925, 2850, 1708, 1450, 990 cm$^{-1}$.

The starting material of the above title compound is produced as follows:

5a) (5R)-5-Acetoxy-1-[cis-(1S)-1-hydroxymethyl)-(2S)-cyclohex-2-yl]-5-cyclohexyl-(1E, 3E)-pentadiene diastereomer pol (12)

A solution of 26 g of dimethyl-(3-cyclohexyl-2-oxo-ethyl)-phosphonate in 283 ml of dimethoxyethane is added in drops to a suspension of 4.03 g of sodium hydride (65% suspension in oil) in 195 ml of dimethoxyethane at 0° C., and it is stirred for 1 hour at 0° C. Then, a solution of the aldehyde, described under 1b, in 470 ml of dimethoxyethane is added in drops, stirred for 1 hour at 0° C., for 4 hours at 25° C. and then poured onto saturated ammonium chloride solution. It is extracted three times with diethyl ether, the organic phase is washed with water, dried on magnesium sulfate and concentrated by evaporation in a vacuum. The residue is purified by column chromatography on silica gel. With hexane/diethyl ether (9+1), 35 g of the unsaturated ketone is obtained as a colorless oil.

IR: 2923, 2850, 1673, 1660, 1630, 1593, 1000, 835 cm$^{-1}$.

To reduce the keto group, 4.95 g of Ce(III)-chloride heptahydrate is added to a solution of 34.6 g of the ketone, described above, in 885 ml of methanol and 89 ml of tetrahydrofuran at –60° C., it is stirred for 15 minutes and then mixed in portions with 5 g of sodium borohydride. It is stirred for 15 minutes at –60° C., mixed with 35 ml of acetone, stirred for 15 minutes, neutralized at room temperature with glacial acetic acid and concentrated by evaporation in a vacuum. Then, the residue is taken up in a diethyl ether/water mixture, the aqueous phase is shaken with diethyl ether, the organic phase is washed neutral with water, dried on sodium sulfate and concentrated by evaporation in a vacuum. The residue is chromatographed several times on silica gel. With hexane/diethyl ether (97+3), first 12 g of the nonpolar S-configured alcohol (5S)-5-hydroxy-1-[cis-(1S)-1-(tert-butyl-dimethylsilyloxymethyl)-(2S)-cyclohex-2-yl]-5-cyclohexyl-(1E, 3E)-pentadiene and 17 g of polar R-configured alcohol (5R)-5-hydroxy-1-[cis-(1S)-1-(tert-butyl-dimethylsilyloxymethyl)-(2S)-cyclohex-2-yl)]-5-cyclohexyl-(1E, 3E)-pentadiene are obtained as colorless oils.

IR: 3340, 2920, 2850, 990, 838 cm$^{-1}$.

Analogously to the acetylation described in Example 1d), 17.4 g of the acetate is obtained as a colorless oil from 17 g of the polar (5R)-configured alcohol, described above.

IR: 2930, 2860, 1725, 1250, 992, 975, 840 cm$^{-1}$.

Analogously to the silyl ether cleavage described in Example 1d), 9.84 g of the alcohol is obtained as a colorless oil from 13 g of the acetate, described above.

IR: 3620, 3450, 2932, 2860, 1725, 1250, 993, 945 cm$^{-1}$.

5b) (5S)-5-Hydroxy-5-[cis-(2S)-2-((1E, 3E)-(5R)-5-acetoxy-5-cyclohexyl-1, 3-pentadiene)-(1S)-cyclohexyl]-pentan-1-ol-tert-butyldimethylsilyl ether (diastereomeripol (12))

Analogously to Example 1e), the aldehyde, which is used without further purification, is obtained from 9.84 g of the alcohol, produced above under 1d, with 77 g of Collins reagent.

Analogously to the Grignard reaction described in Example 1e), first 2.35 g of the 5R-configured diastereomer alcohol is obtained from 6.2 g of the aldehyde, produced above, in the case of chromatographic separation, as well as 5.15 g of the 5S-configured diastereomer alcohol (title compound) as a polar component.

IR: 3570, 2922, 2852, 1729, 1244, 991, 836 cm$^{-1}$.

EXAMPLE 6

(5R)-5-Fluoro-5-[cis-(2S)-2-((1E, 3E)-(5R)-5-hydroxy-5-cyclohexyl-1,3-pentadienyl)-(1S)-cyclohexyl]-pentanoic acid diastereomer pol (12)

Analogously to Example 2, 33 mg of 1-alcohol is obtained as a colorless oil from 560 mg of the (5R)-5-fluoro-5-[cis-(2S)-2-((1E, 3E)-(5R)-5-acetoxy-cyclohexyl-1, 3-pentadienyl)-cyclohexylidene]-pentan-1-ol-tert-butyldimethylsilyl ether and 1.04 g of tetrabutylammonium fluoride, produced in Example 5.

IR: 3420, 2928, 2859, 1737, 1244, 992 cm$^{-1}$.

Analogously to the oxidation of the alcohol to 1-carboxylic acid, described in Example 2, 230 mg of 1-carboxylic acid is obtained as a colorless oil from 330 mg of the alcohol produced above.

IR: 3500, 2930, 2860, 1725, 1248, 992 cm$^{-1}$.

Analogously to the acetate saponification described in Example 2, 218 mg of the title compound is obtained as a colorless oil from 230 mg of the 1-carboxylic acid produced above.

IR: 3480, 2923, 2852, 1737, 1450, 1170, 990, 952, 920 cm$^{-1}$.

EXAMPLE 7

5-[(E)-(2S)-2-((1E, 3E)-(5S)-5-hydroxy-5-cyclohexyl-1, 3-pentadienyl)-cyclohexylidenel]-pentanoic acid diastereomer unpol (12)

Analogously to Examples 1 and 3, the title compound is obtained as a colorless oil from the nonpolar S-configured alcohol (5S)-5-hydroxy-1-[cis-(1S)-1-(tert-butyl-dimethylsilyloxymethyl)-(2S)-cyclohex-2-yl]-5-cyclohexyl-(1E, 3E)-pentadiene that is obtained in Example 5a) after chromatographic separation.

IR: 3400, 2927, 2852, 1708, 1451, 991 cm$^{-1}$.

EXAMPLE 8

(5R)-5-Fluoro-5-[cis-(2S)-2-((1E 3E)-(5S)-5-hydroxy-5-cyclohexyl-1, 3-pentadienyl)-(1S)-cyclohexyl]-pentanoic acid diastereomer unpol (12)

Analogously to Examples 2 and 6, the title compound is obtained as a colorless oil from the (5R)-5-fluoro-5-[cis-(2S)-2-((1E, 3E)-(5S)-5-acetoxy-cyclohexyl-1, 3-pentadienyl)-cyclohexylidene]-pentan-1-ol-tert-butyldimethylsilyl ether that is produced according to Example 5.

IR: 3400, 2925, 2852, 1738, 1450, 1170, 990, 950, 920 cm$^{-1}$.

EXAMPLE 9

5-[(E)-(2S)-2-((1E, 3E)-(5S)-5-Hydroxy-6, 6-trimethylene-9-Phenyl-1, 3-nonadien-8-inyl)-cyclohexylidene]-pentanoic acid-meth yl ester diastereomer pol (12)

An ethereal diazomethane solution is added in drops to a solution of 120 mg of the acid, produced according to Example 1, in 4 ml of dichloromethane at 0° C. until permanent yellow coloring, and it is stirred for 15 minutes at 0° C. Then, it is concentrated by evaporation in a vacuum, and the residue is purified by column chromatography on silica gel. With hexane/ethyl acetate (1+1), 116 mg of the title compound is obtained as a colorless oil.

IR: 3472, 2928, 2853, 2200, 1738, 1442, 1246, 1160, 992 cm$^{-1}$.

EXAMPLE 10

5-[(E)-(2S)-2-((1E, 3E)-(5R)-5-Hydroxy-5-cyclohexyl-1, 3-pentadienyl) -cyclo-hexylidenel]-pientanoic acid methyl ester diastereomer pol (12)

Analogously to Example 9, 160 mg of the title compound is obtained as a colorless oil from 190 mg of the acid produced according to Example 5.

IR: 3470, 2930, 2855, 1739, 992 cm$^{-1}$.

EXAMPLE 11

5-[(E)-(2S)-2-((1E, 3E)-(5S)-5-Hydroxy-6, 6-trimethylene-9-phenyl-1, 3-nonadien-8-inyl)-cyclohexylidene]-pentanoic acid-(3-hydroxypropylamide) diastereomer pol (12)

450 mg of 3-amino-1-propanol is added to a solution of 250 mg of the methyl ester, produced according to Example 9, in 8 ml of acetonitrile, and it is stirred for 24 hours at 50° C. and for 24 hours at 80° C. Then, it is concentrated by evaporation in a vacuum, and the residue is purified by column chromatography on silica gel. With dichloromethane/methanol (9+1), 203 mg of the title compound is obtained as a colorless oil.

IR: 3340, 2928, 2828, 1651, 1530, 990 cm$^{-1}$.

EXAMPLE 12

Tris-(hydroxymethyl)-aminomethane salt of 5-[(E)-(2S)-2-((1E, 3E)-(5S)-5-hydroxy-6, 6-trimethylene-9-phenyl-1, 3-nonadien-8-inyl)-cyclohexylidene]-pentanoic acid diastereomer pol (12)

0.08 ml of an aqueous tris-(hydroxymethyl) aminomethane solution (production: 8.225 g of trishydroxymethyl)aminomethane is dissolved in 15 ml of water) is added to a solution of 150 mg of the carboxylic acid, produced according to Example 1, in 24 ml of acetonitrile at 80° C., it is stirred for 1 hour at 80° C., for 1 hour at 55° C., for 3 hours at 45° C. and for 60 hours at 24° C. The crystals that are produced are suctioned off, washed with some acetonitrile, and the crystals are dried at 24° C. in a vacuum. In this case, 140 mg of the title compound is obtained as a waxy compound.

IR: 3320, 2922, 2852, 1550 (broad), 991 cm$^{-1}$.

EXAMPLE 13

5-[(E)-(2S)-2-((1E, 3E)-(5S)-5-Hydroxy-6, 6-dimethyl-9-phenyl-1, 3-nonadien-8-inyl)-cyclohexylidene]-pentanoic acid diastereomer pol (12)

Analogously to Example 1, 510 mg of 5-[(E)-(2S)-2-((1E, 3E)-(5S)-5-acetoxy-6, 6-dimethyl-9-phenyl-1, 3-nonadien-8-inyl)-cyclohexylidene]-pentan-1-ol-tert-butyldimethylsilyl ether, 390 mg of mixed fractions, is obtained as a nonpolar component from 1.6 g of (5S)-5-hydroxy-5-[cis-(2S)-2-((1E, 3E)-(5S)-5-acetoxy-6, 6-dimethyl-9-phenyl-1, 3-nonadien-8-inyl)-(1S)-cyclohexyl]-pentan-1-ol-tert-butyldimethylsilyl ether (diastereomer pol (12)) and as a polar component, 410 mg of (5R)-5-fluoro-5-[cis-(2S)-2-((1E, 3E)-(5S)-5-acetoxy-6, 6-dimethyl-9-phenyl-1, 3-nonadien-8-inyl)-(1S)-cyclohexyl]-pentan-1-ol-tert-butyldimethylsilyl ether is obtained as a colorless oil.

IR spectrum of the olefin: 2931, 2860, 1730, 1250, 991 cm$^{-1}$.

Analogously to the silyl ether cleavage that is described in Example 1, 280 mg of 1-alcohol is obtained as a colorless oil from 510 mg of the olefin, produced above. In addition, 80 mg of the isomeric Z-configured $\Delta^{5,6}$-olefin is separated here.

IR: 3420, 2925, 2851, 2220, 1736, 1663, 1240, 992 cm$^{-1}$.

Analogously to the oxidation of the 1-hydroxy group that is described in Example 1, 150 mg of 1-carboxylic acid is obtained as a colorless oil from 280 mg of 1-alcohol produced above.

IR: 3510, 2936, 2860, 1729, 1245, 992 cm$^{-1}$.

Analogously to the acetate saponification that is described in Example 1, 122 mg of the title compound is obtained as a colorless oil from 150 mg of the carboxylic acid produced above.

IR: 3410, 2930, 2856, 2220, 1710, 1600, 1490, 991 cm$^{-1}$.

The starting material for the above title compound is produced analogously to the approach described in Example 1a–1e). The 2-oxo-3, 3-dimethyl-6-phenyl-hex-5-ine-phosphonic acid dimethyl ester that is required for the structure of the chain is produced from isobutyric acid, however, analogously to Example 1a).

EXAMPLE 14

(5R)-5-Fluoro-5-[cis-(2S)-2-((1E, 3E)-(5S)-5-hydroxy-6, 6-dimethyl-9-phenyl-1, 3-nonadien-8-inyl)-(1S)-cyclohexyl]-pentanoic acid diastereomer pol (12)

Analogously to Example 2, 260 mg of 1-alcohol is obtained as an oil from 410 mg of the (5R)-5-fluoro-5-[cis-(2S)-2-((1E, 3E)-(5S)-5-acetoxy-6, 6-dimethyl-9-phenyl-1, 3-nonadien-8-inyl)-(1S)-cyclohexyl]-pentan-1-ol-tert-butyldimethylsilyl ether, produced in Example 13, and 810 mg of tetrabutylammonium fluoride. IR: 3450, 2930, 2860, 1740, 1245, 992 cm$^{-1}$.

Analogously to the oxidation of the alcohol, described in Example 2, to 1-carboxylic acid, 180 mg of 1-carboxylic acid is obtained as a colorless oil from 250 mg of the alcohol produced above.

Analogously to the acetate saponification described in Example 2, 145 mg of the title compound is obtained as a colorless oil from 180 mg of 1-carboxylic acid produced above.

3430, 2935, 2863, 2200, 1710, 1599, 992 cm$^{-1}$.

We claim:

1. Leukotriene-B$_4$ derivatives of general formula I,

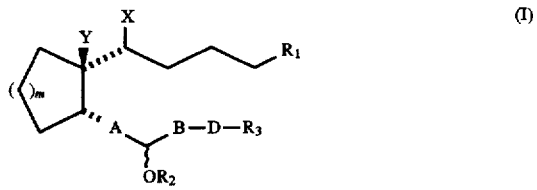

(I)

in which

R$_1$ represents CH$_2$OH, CH$_3$, CF$_3$, COOR$_4$, CONR5R$_6$, and

R$_2$ represents H or an organic acid radical with 1–15 C atoms,

R$_3$ symbolizes H; C$_1$–C$_{14}$ alkyl, C$_3$–C$_{10}$ cycloalkyl optionally substituted singly or multiply; C$_6$–C$_{10}$ aryl radicals, independently of one another, optionally substituted singly or multiply by halogen, phenyl, C$_1$–C$_4$ alkyl, C$_1$–C$_4$ alkoxy, fluoromethyl, chloromethyl, trifluoromethyl, carbonyl, carboxyl or hydroxy; or a 5-to 6-membered aromatic heterocyclic ring with at least 1 heteroatom, R$_4$ means hydrogen, C$_1$–C$_{10}$ alkyl, C$_3$–C$_{10}$ cycloalkyl; C$_6$–C$_{10}$ aryl radicals optionally substituted by 1–3 halogen, phenyl, C$_1$–C$_4$ alkyl, C$_1$–C$_4$ alkoxy, fluoromethyl, chloromethyl, trifluoromethyl, carboxyl or hydroxy; CH$_2$—CO—(C$_6$–C$_{10}$) aryl or a 5- to 6-membered ring with at least 1 heteroatom, A symbolizes a trans, trans—CH=CH—CH=CH, a —CH$_2$CH$_2$—CH=CH— or a tetramethylene group, B symbolizes a $C_1$–$C_{10}$ straight-chain or branched-chain alkylene group, which optionally can be substituted by fluorine or the group

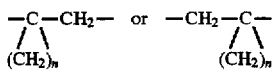

D means a direct bond, oxygen, sulfur, —C≡C—, —CH=CR$_7$, or together with B can also mean a direct bond, $R_5$ and $R_6$ are the same or different, and represent H or $C_1$–$C_4$ alkyl optionally substituted by hydroxy groups or $R_6$ represents H and $R_5$ represents $C_1$–$C_{15}$ alkanoyl or $R_8SO_2$.

$R_7$ means H, $C_1$–$C_5$ alkyl, chlorine, bromine, $R_8$ has the same meaning as $R_3$, m means 1–3, n is 2–5, and, if $R_4$ means hydrogen, their salts with physiologically compatible bases and their cyclodextrin clathrates, X and Y mean a direct bond, whereby the resulting olefin can be E- or Z-configured or X represents a fluorine atom in α- or β-position, and Y means a hydrogen atom in β-position.

2. Pharmaceutical preparations characterized by a content of leukotriene-$B_4$ derivatives of general formula I according to claim 1.

3. Process for the production of leukotriene-$B_4$ derivatives of general formula I, according to claim 1, characterized in that an alcohol of formula II

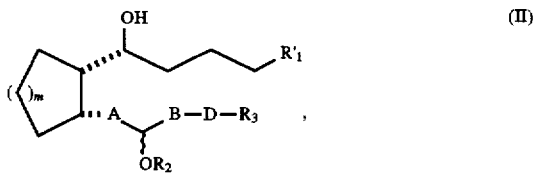

in which A, B, D, $R_1$, $R_2$ and $R_3$ have the above-indicated meaning and $R'_1$ has the same meaning as $R_1$ or represents grouping —$CH_2OR_9$, in which $R_9$ means a readily cleavable ether radical, optionally under protection of free hydroxy groups in $R_2$, is reacted with a dehydrating reagent or fluorinating reagent of general formula III,

whereby Alk represents —$CH_3$ or —$CH_2CH_3$, optionally in the presence of a base and then optionally is separated in any sequence of isomers, protected hydroxy groups are released and/or a free hydroxy group is esterified and/or the 1-hydroxy group is oxidized to carboxylic acid and/or double bonds are hydrogenated and/or an esterified carboxyl group is saponified and/or reduced and/or a carboxyl group is esterified and/or a free carboxyl group is converted to an amide or a carboxyl group is converted to a salt with a physiologically compatible base.

* * * * *